(12) United States Patent
Kelly et al.

(10) Patent No.: US 10,576,475 B2
(45) Date of Patent: Mar. 3, 2020

(54) DIAGNOSTIC ASSAY STRIP CASSETTE

(71) Applicant: GENPRIME, INC., Spokane, WA (US)

(72) Inventors: Connor S. Kelly, Sammamish, WA (US); Darby Dawn McLean, Spokane Valley, WA (US); Jason Buck Somes, Spokane, WA (US)

(73) Assignee: GENPRIME, INC., Spokane, WA (US)

( * ) Notice: Subject to any disclaimer, the term of this patent is extended or adjusted under 35 U.S.C. 154(b) by 341 days.

(21) Appl. No.: 15/705,461

(22) Filed: Sep. 15, 2017

(65) Prior Publication Data

US 2018/0071741 A1 Mar. 15, 2018

Related U.S. Application Data

(60) Provisional application No. 62/395,150, filed on Sep. 15, 2016.

(51) Int. Cl.
*B01L 9/00* (2006.01)
*G01N 35/00* (2006.01)

(52) U.S. Cl.
CPC .......... *B01L 9/52* (2013.01); *G01N 35/00029* (2013.01); *B01L 2200/025* (2013.01);
(Continued)

(58) Field of Classification Search
CPC ................ B01L 9/52; B01L 2200/025; B01L 2300/0809; B01L 2300/041;
(Continued)

(56) References Cited

U.S. PATENT DOCUMENTS

| 4,103,287 A | 7/1978 | Frank |
| 4,718,090 A | 1/1988 | Cooper, Jr. |

(Continued)

FOREIGN PATENT DOCUMENTS

| EP | 0 953 149 B1 | 9/2004 |
| WO | 00/46598 A1 | 8/2000 |

OTHER PUBLICATIONS

Extended European Search Report for corresponding European Application No. 09808610.1, dated Jan. 30, 2013, 10 pages.
(Continued)

*Primary Examiner* — Dennis White
(74) *Attorney, Agent, or Firm* — Cozen 'Connor

(57) ABSTRACT

A cassette removably holds assay strips. The cassette includes a cover and a base. The base includes a first face and a second face, the second face opposed across a thickness of the base from the first face. The base has at least a first channel in the first face that extends along at least a portion of the base, the at least first channel having a width, a length and a depth, at least the width and the depth of the first channel sized to at least partially receive an assay strip therein. The cover has a first face and a second face, the second face opposed across a thickness of the cover from the first face. The cover is releasably securable to the base in at least two orientations to alternatively expose a first set of markings and a second set of markings. The first and the second set of markings are carried by at least one of the cover or the base. The first set of markings is indicative of a first type of assay strip and the second set of markings is indicative of a second type of assay strip; the second set of markings being different from the first set of markings. The two different orientations include a first orientation in which the first face of the cover is exposed and the second face of the cover is adjacent one of the first or the second faces of the base, and a second orientation in which the second face of the cover is exposed and the first face of the cover is adjacent one of the first or the second faces of the base.

24 Claims, 8 Drawing Sheets

(52) U.S. Cl.
CPC ..... *B01L 2200/14* (2013.01); *B01L 2200/141* (2013.01); *B01L 2300/021* (2013.01); *B01L 2300/041* (2013.01); *B01L 2300/0809* (2013.01); *G01N 2035/00108* (2013.01); *G01N 2035/00287* (2013.01)

(58) Field of Classification Search
CPC ......... B01L 2300/021; B01L 2200/141; B01L 2200/14; G01N 35/00029; G01N 2035/00287; G01N 2035/00108
See application file for complete search history.

(56) References Cited

U.S. PATENT DOCUMENTS

| | | | |
|---|---|---|---|
| 5,403,551 | A | 4/1995 | Galloway et al. |
| 5,408,535 | A | 4/1995 | Howard, III et al. |
| 5,429,804 | A | 7/1995 | Sayles |
| 5,569,608 | A | 10/1996 | Sommer |
| 5,707,797 | A | 1/1998 | Windle |
| 6,136,549 | A | 10/2000 | Feistel |
| 6,165,734 | A | 12/2000 | Garini et al. |
| 6,248,596 | B1 | 6/2001 | Durst et al. |
| 6,404,906 | B2 | 6/2002 | Bacus et al. |
| 6,416,959 | B1 | 7/2002 | Giuliano et al. |
| 6,436,721 | B1 | 8/2002 | Kuo et al. |
| 6,607,922 | B2 | 8/2003 | LaBorde |
| 6,671,624 | B1 | 12/2003 | Dunlay et al. |
| 6,936,476 | B1 | 8/2005 | Anderson et al. |
| 7,020,307 | B2 | 3/2006 | Hinton et al. |
| 7,117,098 | B1 | 10/2006 | Dunlay et al. |
| 7,267,799 | B1 | 9/2007 | Borich et al. |
| 7,323,139 | B2 | 1/2008 | LaBorde et al. |
| 7,330,606 | B2 | 2/2008 | Yakhini et al. |
| 7,371,582 | B2 | 5/2008 | Nahm et al. |
| 7,390,675 | B2 | 6/2008 | Feistel |
| 7,403,661 | B2 | 7/2008 | Curry et al. |
| 7,444,005 | B2 | 10/2008 | Bachur, Jr. et al. |
| 7,526,114 | B2 | 4/2009 | Xia et al. |
| 7,818,130 | B2 | 10/2010 | Sipe et al. |
| 7,910,873 | B2 | 3/2011 | Lue et al. |
| 7,940,968 | B2 | 5/2011 | Seul et al. |
| 7,957,911 | B2 | 6/2011 | Harris et al. |
| 8,059,893 | B2 | 11/2011 | Prusia |
| 8,117,071 | B1 | 2/2012 | Fitch et al. |
| 8,446,463 | B2 | 5/2013 | Fleming et al. |
| 8,698,881 | B2 | 4/2014 | Fleming et al. |
| 2002/0009389 | A1 | 1/2002 | Lappe et al. |
| 2002/0009390 | A1 | 1/2002 | Lappe et al. |
| 2002/0031783 | A1 | 3/2002 | Empedocles et al. |
| 2002/0159625 | A1 | 10/2002 | Elling |
| 2003/0036096 | A1 | 2/2003 | Ravkin et al. |
| 2003/0036855 | A1 | 2/2003 | Harris et al. |
| 2003/0039384 | A1 | 2/2003 | Bacus et al. |
| 2003/0040031 | A1 | 2/2003 | Kim et al. |
| 2003/0156739 | A1 | 8/2003 | Hinton et al. |
| 2003/0190075 | A1 | 10/2003 | Averbuch et al. |
| 2004/0033610 | A1 | 2/2004 | Lovell et al. |
| 2004/0101912 | A1 | 5/2004 | Rubin et al. |
| 2004/0146917 | A1 | 7/2004 | Cork et al. |
| 2004/0264807 | A1 | 12/2004 | Yakhini et al. |
| 2005/0008212 | A1 | 1/2005 | Ewing et al. |
| 2005/0180642 | A1 | 8/2005 | Curry et al. |
| 2005/0180647 | A1 | 8/2005 | Curry et al. |
| 2005/0203353 | A1* | 9/2005 | Ma .......................... G01N 21/01 600/315 |
| 2006/0039603 | A1 | 2/2006 | Koutsky |
| 2006/0062440 | A1 | 3/2006 | Hollars et al. |
| 2006/0072817 | A1 | 4/2006 | Lee et al. |
| 2006/0172280 | A1 | 8/2006 | Kim et al. |
| 2006/0222227 | A1 | 10/2006 | Seul et al. |
| 2006/0275799 | A1 | 12/2006 | Banerjee et al. |
| 2006/0292040 | A1 | 12/2006 | Wickstead et al. |
| 2008/0123945 | A1 | 5/2008 | Andrew et al. |
| 2008/0181482 | A1 | 7/2008 | Bouchard et al. |
| 2008/0260233 | A1 | 10/2008 | Hays et al. |
| 2008/0304723 | A1 | 12/2008 | Hsieh et al. |
| 2009/0068064 | A1 | 3/2009 | Gordon |
| 2009/0208104 | A1 | 8/2009 | Prusia |
| 2010/0033724 | A1 | 2/2010 | Cork et al. |
| 2010/0045789 | A1 | 2/2010 | Fleming et al. |
| 2010/0239137 | A1 | 9/2010 | Pugia et al. |
| 2011/0255756 | A1 | 10/2011 | Harris et al. |
| 2013/0330831 | A1 | 12/2013 | Morrow et al. |
| 2015/0211987 | A1 | 7/2015 | Burg et al. |
| 2016/0080548 | A1 | 3/2016 | Erickson et al. |
| 2016/0225165 | A1 | 8/2016 | Russell et al. |

OTHER PUBLICATIONS

International Search report for corresponding International Application No. PCT/US2009/053404, dated Apr. 6, 2010, 3 pages.
Written Opinion for corresponding International Application No. PCT/US2009/053404, dated Apr. 6, 2010, 7 pages.
Fleming et al., "Apparatus, Method and Article to Perform Assays Using Strips," Amendment for U.S. Appl. No. 12/538,716, filed Jun. 19, 2012, 60 pages.
Fleming et al., "Apparatus, Method and Article to Perform Assays Using Strips," Amendment After Final for U.S. Appl. No. 12/538,716, filed Dec. 28, 2012, 10 pages.
Fleming et al., "Apparatus, Method and Article to Perform Assays Using Strips," Office Action for U.S. Appl. No. 12/538,716, dated Mar. 20, 2012, 23 pages.
Fleming et al., "Apparatus, Method and Article to Perform Assays Using Strips," Office Action for U.S. Appl. No. 12/538,716, dated Oct. 5, 2012, 19 pages.
Haralick et al., "Image Segmentation Techniques," *Computer Vision, Graphics, and Image Processing* 29:100-132, 1985.
Russell et al., "System and Method to Interpret Tests That Change Color to Indicate the Presence or Non-Presence of a Compound," U.S. Appl. No. 62/369,588, filed Aug. 1, 2016, 51 pages.

* cited by examiner

__US 10,576,475 B2__

DIAGNOSTIC ASSAY STRIP CASSETTE

TECHNICAL FIELD

The present disclosure generally relates to a cassette for use with diagnostic assay strips and, more particularly, to a cassette that provides at least two distinct sets of human and/or machine-readable indicia selectively orientable and hence viewable for use with respective types of diagnostic assay strips.

BACKGROUND

Description of the Related Art

Specimen assay or test articles such as diagnostic assay or test strips may be used to determine a presence or absence of an assay or test subject substance in a specimen (i.e., the principal substance for which the specimen is being assayed or tested). In particular, certain specimen assay articles (e.g., lateral flow strips, dipsticks) include at least one optical assay substance marker that optically indicates at least the presence or absence of the assay subject substance in the specimen. For example, a visually detectable appearance or absence of one or more optical assay substance markers may indicate the presence or absence of the assay subject substance within the specimen. For instance, a presence of a assay subject substance may be indicated by a visual line on a diagnostic assay strip, where the line would not otherwise be visually detectable in absence of the assay subject substance. Also for example, a color of one or more optical assay substance markers may indicate the presence or absence of the assay subject substance within the specimen. For instance, a color of an optical assay substance marker may remain unchanged from a first color if the specimen does not contain the assay subject substance, while the color of the optical assay substance marker changes from the first color to a second, different color if the assay subject substance is present within the specimen.

Specimen assay or test articles may also include one or more optical specimen validity markers, in addition to the optical assay substance marker. A visual presence or absence, or alternatively a color of the optical specimen validity marker indicates a validity of the specimen. As one example, the optical specimen validity marker may change colors in the presence of an adulterant, where the presence of an adulterant renders the specimen invalid. As another example, the optical specimen validity marker may remain the same color in the absence of a particular substance in the specimen, where the absence of the particular substance in the specimen renders the specimen invalid. As yet another example, the optical specimen validity marker may change colors to indicate a value or status of a physical characteristic of the specimen, such as pH, specific gravity, temperature, or other characteristics. The validity of the specimen may be inferable or determinable in view of the indicated value or status of the physical characteristic.

Specimen assay or test articles may also include a control marker that simply indicates whether the specimen assay or test article properly absorbed or otherwise received the specimen.

A human tester using the specimen assay or test article to assay or test for the assay subject substance may manually view the specimen assay or test article and attempt to determine the assay or test results. However, this requires the human tester to manually determine the presence and/or absence of lines, the respective colors of the assay substance marker and the specimen validity marker and to manually determine the results of the assay or test from such presence and/or absence and/or colors. Such process may result in an undesirably high number of errors. For example, the human tester may incorrectly interpret the color of one or more markers, particularly for markers that provide a plurality or a spectrum of colors which indicate different results. As another example, the human tester may confuse one marker for another or otherwise incorrectly translate the colors of the markers into results of the test.

BRIEF SUMMARY

Specimen analysis systems that automate the reading and interpretation of assess specimen assay or test articles (e.g., diagnostic test or assay strips, such as lateral flow strips, dipsticks) are desirable.

Applicants have recognized that it would be advantageous to employ a cassette to hold assay or test articles (e.g., diagnostic test or assay strips, such as lateral flow strips, dipsticks) for scanning and/or reading of the diagnostic test strips by a specimen analysis system or machine reader. In particular, failing to use a cassette can result in a number of problems. First, there can be cross contamination between the assay or test articles (e.g., diagnostic test or assay strips) and a surface of the specimen analysis system or machine reader. Second, absent using a cassette, it can be difficult to hold the assay or test articles (e.g., diagnostic test or assay strips)in place and at the proper position and orientation (in three-dimensions) for an accurate imaging by the specimen analysis system or machine reader. Third, absent using a cassette, it may be difficult to provide the necessary human- and/or machine-readable indicia or markings since many diagnostic testing strips are small and do not have sufficient available surface area to carry such information.

Therefore, there is a need for a cassette for use with assay or test articles (e.g., diagnostic test or assay strips); the cassette having one or more channels dimensioned to receive a diagnostic strip test; the cassette holding the diagnostic test strip flush and/or parallel to an image plane of the optics of specimen analysis system or machine reader; the cassette preventing contact between the assay or test articles and the surfaces of the specimen analysis system or machine reader to mitigate cross contamination; and to provide sufficient surface are to provide human- and/or machine-readable markings or information that related to the assay or test articles.

Briefly, and in general terms, there is disclosed a cassette enclosure for use with assay or test articles (e.g., diagnostic test or assay strips). The cassette enables selective display of alternative human- and/or machine-readable markings or information based on the type of assay or test articles (e.g., diagnostic test or assay strips) loaded into the cassette. More particularly, an assay or test articles (e.g., diagnostic test or assay strips) is housed within a channel contained in a base of the cassette. A cassette cover, having multiple orientations (e.g., first major face exposed, second major face exposed) to provide one of a plurality of sets of human- and/or machine-readable markings or information is secured to the base of the cassette, in alignment and/or registration with at least some of the human- and/or machine-readable markings or information, preferably adjacent the channel. By selecting the particular orientation of the cover when placed upon the base of the cassette, different human- and/or machine-readable markings or information are exposed, and thus can be imaged by the specimen analysis system or machine reader. The orientation of the cover relative to the base can advantageously be determined at time of use, for example when the assay or test article is being loaded in the cassette. This can advantageously allow reading from two or more types of assay or test article (e.g., 5 line diagnostic test or assay strip, 10 line diagnostic test or assay strip) by the same specimen analysis system or machine reader. As noted, some of the human- and/or machine-readable markings or information can be arrayed adjacent to and aligned with various portions of the assay or test articles (e.g., diagnostic test or assay strips) residing in the channel of the base of the cassette. Different human- and/or machine-readable markings or information can provide different testing information regarding the type of assay test strip in use. The cover may be removably secured to the base, for example via one or more magnets, or other releasable couplers, for example allowing the cassette to be reused. Alternatively, cover may be permanently secured to the base, particularly for disposable single use cassettes, A cassette to removably hold assay strips may be summarized as including: a base, the base having a first face and a second face, the second face opposed across a thickness of the base from the first face, the base having a first channel in the first face that extends along at least a portion of the base, the first channel having a width, a length and a depth, at least the width and the depth of the first channel sized to closely removably receive an assay strip therein; and a cover, the cover having a first face and a second face, the second face opposed across a thickness of the cover from the first face, the cover releasably securable to the base in at least two orientations to alternatively expose a first set of markings and a second set of markings, the first and the second set of markings carried by at least one of the cover or the base, the first set of markings indicative of a first type of assay strip and the second set of markings indicative of a second type of assay strip, the second set of markings different from the first set of markings, the two orientations including a first orientation in which the first face of the cover is exposed and the second face of the cover is adjacent one of the first or the second faces of the base, and a second orientation in which the second face of the cover is exposed and the first face of the cover is adjacent one of the first or the second faces of the base.

The base may have a length and a width, and the first channel may extend along the length of the base and may be centered with respect to the width of the base. The cover may have a window and an opaque frame about the window, the window transparent to light of at least one range of wavelengths, and the first set of markings may be carried on the first face of the cover and the second set of markings may be carried on the second face of the cover. The window of the cover may be in registration with the first channel when the cover is releasably secured to the base in both the first and the second orientations. The base may have a length and a width, and may have a second channel in the first face of the base that extends along at least a portion of the length of the base, the second channel having a width, a length and a depth, at least the width and the depth of the second channel sized to closely removably receive an assay strip therein, the first channel laterally disposed in a first direction from a centerline of the base and the second channel laterally disposed in a second direction from the centerline of the base, the second direction opposite the first direction. The cover may have a window and an opaque frame about the window, the window transparent to light of at least one range of wavelengths, and the first set of markings may be carried on the first face of the cover and the second set of markings may be carried on the second face of the cover, the window spaced relatively towards a first lateral edge of the cover with respect to a second lateral edge of the cover, the second lateral edge of the cover opposed across a width of the cover from the first lateral edge of the cover. The window of the cover may be in registration with the first channel when the cover is releasably secured to the base in the first orientation, and the window of the cover may be in registration with the second channel when the cover is releasably secured to the base in the second orientation. The base may have a length and a width, and may have a second channel in the second face of the base that extends along at least a portion of the length of the base, the second channel having a width, a length and a depth, at least the width and the depth of the second channel sized to closely removably receive an assay strip therein, the first channel laterally disposed in a first direction from a centerline of the base and the second channel laterally disposed in a second direction from the centerline of the base, the second direction opposite the first direction. The cover may be transparent to light of at least one range of wavelengths, and the first set of markings may be carried on the first face of the base and the second set of markings may be carried on the second face of the base. The first set of markings may be carried on the first face of the base, a number of the first set of markings spaced laterally to a first side of the first channel, and the second set of markings may be carried on the first face of the base, a number of the second set of markings spaced laterally to a second side of the first channel, the second side opposed across the first channel from the first side of the first channel. The cover may have a window and an opaque frame about the window, the window transparent to light of at least one range of wavelengths, and the window laterally disposed in a first direction from a centerline of the cover. The window of the cover may be in registration with the first channel and the number of the first set of markings that are spaced laterally to the first side of the first channel when the cover is releasably secured to the base in the first orientation to expose the first channel and the number of the first set of markings and occlude the number of the second set of markings in the first orientation, and the window of the cover may be in registration with the first channel and the number of the second set of markings that are spaced laterally to the second side of the first channel when the cover is releasably secured to the base in the second orientation to expose the first channel and the number of the second set of markings and occlude the number of the first set of markings in the second orientation. The first set of markings may include a first number of markings that extend along at least a portion of the window and which align with respective portions of the first type of assay strip when the first type of assay strip is received in the first channel, and the second set of markings may include a second number of markings that extend along at least a portion of the window and which align with respective portions of the second type of assay strip when the second type of assay strip is received in the first channel. The first set of markings may include a number of human-readable markings that are laterally offset to a first side of the window and the second number of markings may include markings that are laterally offset to a second side of the window, the second side opposed across the window from the first side. The first set of markings may include a number of human-readable markings that are laterally offset to a first side of the window and the second number of markings may include markings that are laterally offset to a second side of the window, the second side opposed across the window from the first side. The first set of markings may include a first machine-readable symbol that encodes a first set of machine-readable information, and the second set of markings may include a second machine-readable symbol that encodes a second set of machine-readable information, the second set of machine-readable information different from the first set of machine-readable information. The cover may be a transparent substrate and the frame may be an opaque layer carried by the transparent substrate, and the window may provide environmental protection to an assay strip removably received in the first channel. The cassette may further include: a plurality of magnetic elements, at least one of the magnetic elements carried by the base and at least one of the magnetic elements carried by the cover, the magnetic elements carried by the base arranged with respect to the magnetic elements carried by the cover to magnetically releasably retain the cover to the base. The cassette may further include: a plurality of magnetic elements, at least one of the magnetic elements carried by the base and at least one of the magnetic elements carried by the cover, the magnetic elements carried by the base arranged with respect to the magnetic elements carried by the cover to magnetically releasably retain the cover to the base only in the first and the second orientations, and not in any other orientation, where: i) in the first orientation, a plurality of markings of the first set of markings align with respective indication lines of a first type of assay strip, and ii) in the second orientation, a plurality of markings of the second set of markings align with respective indication lines of a second type of assay strip, the second type of assay strip having a fewer total number of indication lines than a total number of indication lines of the first type of assay strip. The plurality of magnetic elements may include a number of magnets. The plurality of magnetic elements may include a number of pieces of ferrous metal. The base may be a rectangular substrate with a length and a width, and the cover may be a rectangular substrate with a length and a width, the length and the width of the cover being respectively equal to the length and the width of the base. The first channel may extend to an end of the base and the length of the first channel may be sized such that a portion of an assay strip received in the first channel extends partially outward from the end of the base.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not necessarily drawn to scale, and some of these elements may be arbitrarily enlarged and positioned to improve drawing legibility. Further, the particular shapes of the elements as drawn, are not necessarily intended to convey any information regarding the actual shape of the particular elements, and may have been solely selected for ease of recognition in the drawings.

DETAILED DESCRIPTION

Figure 1:
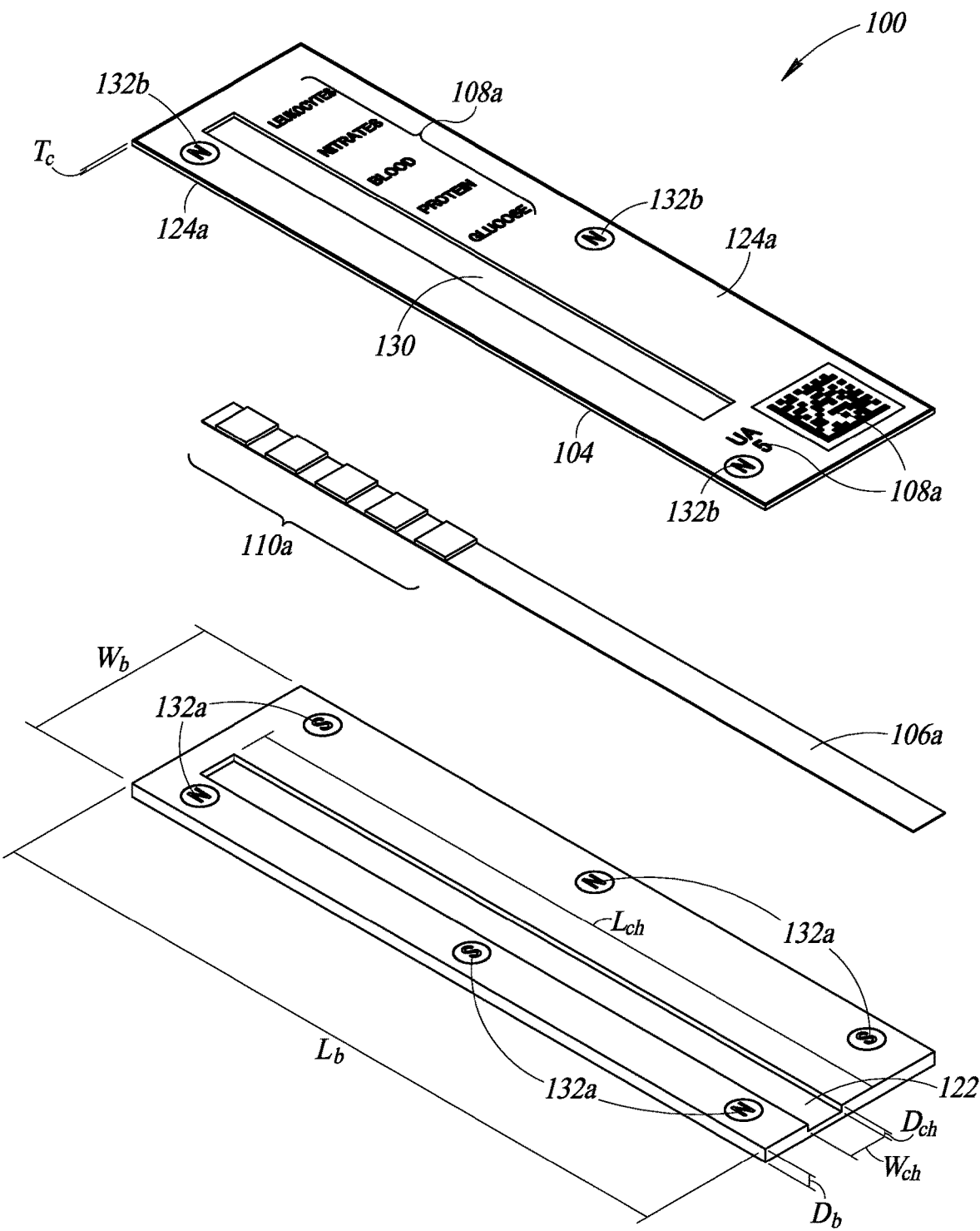
FIG. 1 is an isometric view of a cassette and a first type of diagnostic test or assay test strip, the cassette including a base with a central channel and a cover with a central window, shown with the cover in a first orientation with a first set of human- and/or machine-readable markings or information visible and with at least some of the first set of human- and/or machine-readable markings or information aligned with respective portions of a first type of diagnostic assay test strip, according to at least one illustrated embodiment.

Generally, a cassette includes a base and a cover, the base having at least one enclosure channel sized and dimensioned to hold a test strip during a testing cycle. The cassette provides a barrier between the reagent pads on the test strip and the testing surface of a testing device, thus preventing cross contamination during multiple test sequences. The cassette may be a disposable single use cassette or designed for multiple uses including withstanding repeated cleansing cycles. The cover of the cassette is removable for easy cleaning and to visually expose different sets of testing indicia when the cover is placed upon the base of the cassette. The cover may be placed upon the base of the cassette in one of a plurality of orientations. Each orientation enables the display of a different set of testing indicia adjacent to the test strip. The visible indicia may be carried or inscribed on the cover, the base or a combination thereof. A window in the cover enables the test strip to be viewed during the testing process, along with the testing indicia being used. The window can provide environmental protection while being transparent to at least some wavelengths of electromagnetic energy (e.g. light). Magnets or other suitable connectors (e.g., releasable connectors) ensure that the proper orientation of the cover relative to the base and the test strip is used with each test strip for proper analysis.

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures and methods (e.g., various components of computing devices, principles of operation of a lateral flow strip, etc.) have not been shown or described in detail to avoid unnecessarily obscuring descriptions of the embodiments.

Unless the context requires otherwise, throughout the specification and claims that follow, the word "comprising" is synonymous with "including," and is inclusive or open-ended (i.e., does not exclude additional, unrecited elements or method acts).

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the context clearly dictates otherwise. It should also be noted that the term "or" is generally employed in its broadest sense, that is, as meaning "and/or" unless the context clearly dictates otherwise.

The headings and Abstract of the Disclosure provided herein are for convenience only and do not interpret the scope or meaning of the embodiments.

FIG. 1 shows a cassette 100 having a base 102 and a cover 104 for use with a first type of diagnostic assay test strip (e.g., 5 line test strip) 106a, the cover 104 in a first orientation with respect to the base 102 with a first set of human- and/or machine-readable markings or information, collectively 108a, visible and with at least some of the first set of human- and/or machine-readable markings or information aligned with respective portions, collectively 110a, of the first type of diagnostic assay test strip 106a, according to at least one illustrated embodiment.

Figure 2:
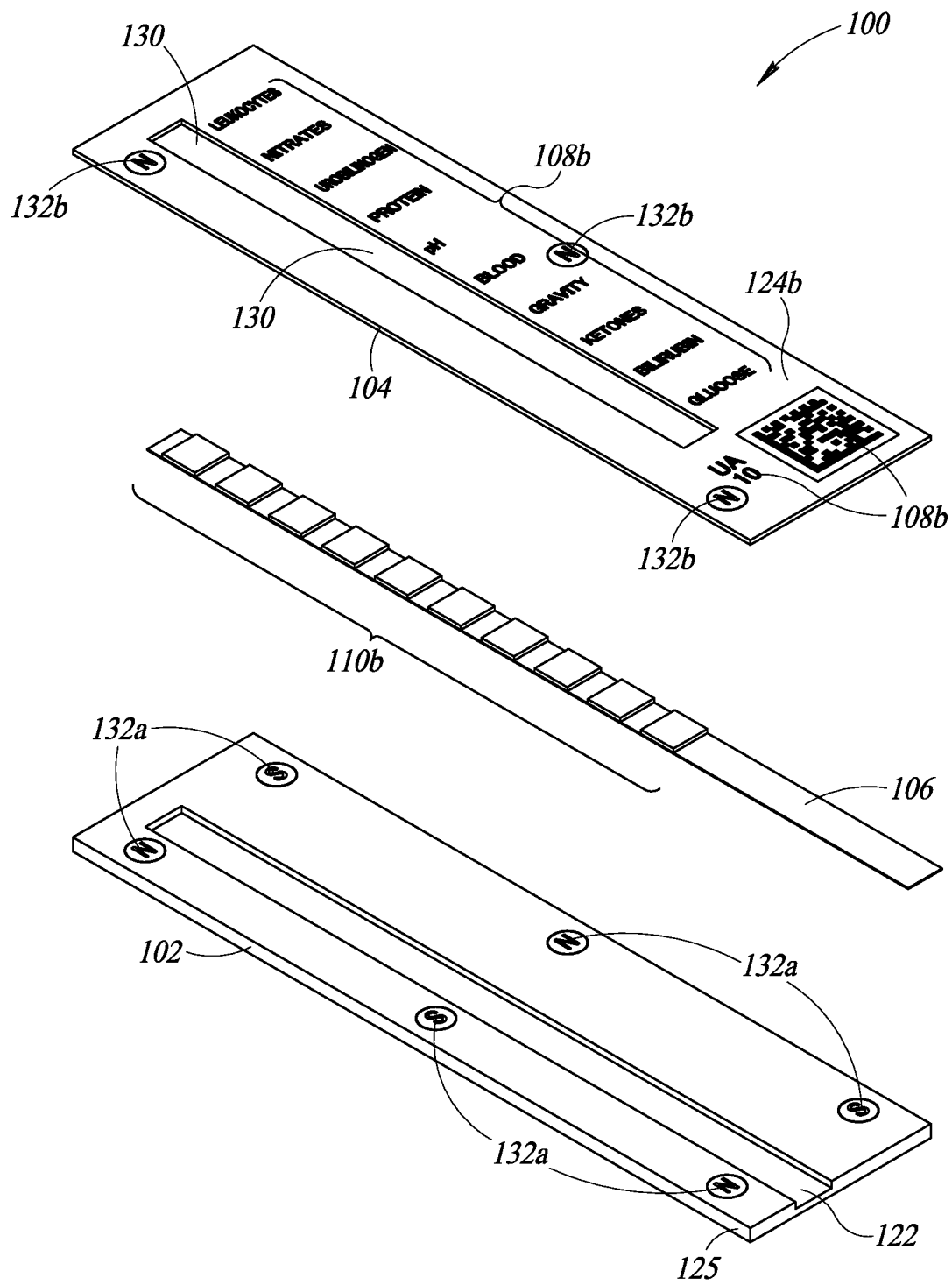
FIG. 2 is an isometric view of the cassette of FIG. 1, and a second type of diagnostic assay test strip, shown with the cover in a second orientation with a second set of human- and/or machine-readable markings or information visible and with at least some of the second set of human- and/or machine-readable markings or information aligned with respective portions of a second type of diagnostic assay test strip, according to at least one illustrated embodiment.

FIG. 2 shows the cassette 100 for use with a second type of diagnostic assay test strip (e.g., 10 line test strip) 106b, the cover 104 in a second orientation with respect to the base 102, with a second set of human- and/or machine-readable markings or information, collectively 108b, visible and with at least some of the second set of human- and/or machine-readable markings or information aligned with respective portions, collectively 110b, of the second type of diagnostic assay test strip 106b.

With reference to FIGS. 1 and 2, the cover 104 is advantageously selectively attachable to the base 102 in a desired orientation, for example, by an end user at a time when the is loaded in the cassette 100 (e.g., after manufacture of the cassette). In some implementations, the cover 104 is removably attachable to the base 102, for example allowing reuse of the cassette 100, for instance after sanitization or sterilization.

The diagnostic assay test strips 106a, 106b can take a variety of forms. For example, one diagnostic assay test strips 106a can take the form of a 5 line test strip, with 5 distinct positons, collectively 110a, each position with a respective reagent responsive to a respective assay subject substance to test for a presence or absence of the respective assay subject substance. Also for example, one diagnostic assay test strips 106b can take the form of a 10 line test strip, with 10 distinct positons, collectively 110b, each position with a respective reagent responsive to a respective assay subject substance to test for a presence or absence of the respective assay subject substance.

The base 102 can take the form of a substrate, having a first face 120a and a second face 120b. The second face 120b is positioned across a thickness $T_b$ of the base 102 across from the first face 120a. The base 102 can be comprised of any of a large variety of materials, and will typically comprise a polymer, for example a plastic. The base 102 includes at least a channel 122 positioned in the first face 120a of the base, the channel 122 extending along at least a portion (e.g., length) $L_b$ of the base 102. While the channel 122 is illustrated as positioned offset to one side or the other of a centerline of the base 102 in other implementations, the channel 112 can be positioned centrally with respect to a width $W_b$ of the base 102. The first channel 122 has a width $W_{ch}$, a length $L_{ch}$ and a depth $D_{ch}$, with at least the width $W_{ch}$ and the depth $D_{ch}$ of the channel 122 sized and dimensioned to closely receive the diagnostic assay test strips 106a, 106b therein. In at least some implementations, the channel 122 is sized and dimensioned to closely removably receive the diagnostic assay test strips 106a, 106b therein. As illustrated in FIGS. 1 and 2, the channel 122 may extend through an end 125 of the base 102, such that an end portion of the diagnostic assay test strip 106a, 106b extends from the cassette 100 when loaded therein.

The cover 104 can take the form of a substrate, having a first face 124a and a second face 124b. The second face 124b of the cover 120 is positioned across a thickness $T_c$ of the cover 106 from the first face 124a. The cover 120 may be a transparent substrate 126, with an opaque layer 128 carried on one face 124a, or opaque layers 128 carried on both faces of the transparent substrate 126, and with a window 130 formed in the opaque layer(s) 128. The window 130 and transparent substrate 126 are transparent to light of at least one range of wavelengths allowing imaging of the diagnostic assay test strip 106a, 106b. The window 130 may provide environmental protection between the diagnostic assay test strip 106a, 106b received in the channel 122 and surfaces of a specimen analysis system or machine reader and/or the external environment.

As illustrated in FIG. 1, the first face 124a of the cover 104 bears a first set of human- and/or machine-readable markings or information 108a, which can be printed or otherwise inscribed on the opaque layer 128. As illustrated in FIG. 2, the second face 124b of the cover 104 bears a second set of human- and/or machine-readable markings or information 108b, which can be printed or otherwise inscribed on the opaque layer 128. The second set of human- and/or machine-readable markings or information 108b is different from the first set of human- and/or machine-readable markings or information 108a. For example, the first set of human- and/or machine-readable markings or information 108a may be specific to a first type of diagnostic assay test strip 106a, for instance including respective identifiers for specific assays or tests and otherwise identifying the type of diagnostic assay test strip 106a. Also for example, the second set of human- and/or machine-readable markings or information 108b may be specific to a second type of diagnostic assay test strip 106b, for instance including respective identifiers for specific assays or tests and otherwise identifying the type of diagnostic assay test strip 106b. At least some of the human- and/or machine-readable markings or information 108a, 108b (e.g., respective identifiers for specific assays or tests) may be positioned along the window 130 to align with respective portions of the diagnostic assay test strip 106a, 106b when the cover 104 is placed on the base 102 in a desired or selected or correct orientation (e.g., first face exposed/second face adjacent the base, second face exposed/first face adjacent the base). Other the human- and/or machine-readable markings or information 108a, 108b (e.g., type identifier, machine-readable barcode or 2-D code symbol) may not be aligned with any specific portions of the diagnostic assay test strip 106a, 106b. For example, if a 5 reagent urinalysis assay test strip 106a is used, then the corresponding cover 104 may include indicia indicating that a 5 UA test is in use and what each reagent pad is testing. Alternatively, if a 10 reagent urinalysis assay test strip 106b is used, then the cover 104 is re-oriented to show different indicia relevant to the 10 UA test.

The two orientations include a first orientation in which the first face 124a of the cover 104 is exposed and the second face 124b of the cover 104 is adjacent one of the first or the second faces 120a, 120b of the base 102. In a second orientation, the second face 124b of the cover 104 is exposed and the first face 124a of the cover 104 is adjacent one of the first or the second faces 120a, 120b of the base 102. In each of the first and the second orientations, the window 130 is in registration with the channel 122, thereby exposing the relevant portions of the diagnostic assay test strip 106a, 106b.

As illustrated, various magnetic elements (i.e., magnets, ferrous metal) 132a, 132b are positioned on the base 102 and cover 104, respectively, which properly align the cover 104 with respect to the base 102 in each of correct or acceptable orientations of the cover 120 with respect to the base 102. In particular, the magnetic elements 132a on the base 102 and the magnetic elements 132b on cover 104 are positioned and magnetic poles orientated such that the cover 104 only attaches to the base 102 in select orientations, e.g., with the window 130 of the cover 104 aligned with the channel 122 of the base 102 and with at least some of the respective set of human- and/or machine-readable markings or information 108a, 108b aligned with respective portions of the of diagnostic assay test strip 106a, 106b. While illustrated with magnetic elements 132a, 132b, other implementations can employ other types of attachment and registration mechanisms, including snap on or click together components, pins and apertures, adhesives or hook and loop fastener Velcro® (with single use cassettes) and the like.

The cassette channel 100 is constructed to enable the diagnostic assay test strip 106a, 106b to remain positioned therein during automated assaying testing. The cassette 100 can be constructed for a single use or it can be manufactured for multiple uses. Whether for a single use or a multiple use, the cassette 100 may be constructed using any appropriate material, e.g., plastic, glass, polymers, resins, metal, and the like. However, if the cassette 100 is constructed for multiple uses, then the materials must be capable of withstanding any required cleansing or sterilization process, e.g., autoclaving or chemical sterilization.

The cassette 100 can be constructed for use with most, if not all, standard sized testing strips. The cassette 100 is rectangular in shape having a base length $L_b$ of 9.5 cm, a base width $W_b$ of 2.5 cm and a base thickness $T_b$ of 0.4 cm. The channel 122 that extends along a portion of the base 102 and has a channel width $W_{ch}$ of 0.5 cm and a channel depth $D_{ch}$ of 0.2 cm. The channel 122 can be centered within the base 102 as illustrated in FIGS. 1 and 2. The assay test strip 106 resides within the channel 122 during use. As previously described, a plurality of magnetic elements 132a, 132b may located on the base 102 and are offset 0.2 cm from the top, bottom and sides of the base 102. The polarity of each magnet element 132a, 132b may be indicated by an "S" or an "N."

The cover 104 corresponds in length and width to the base 102. The cover 104 includes a window cut 130 having a width of 0.5 cm that allows visibility of the diagnostic assay test strip 106a, 106b, residing within the channel 122. The cover 104 has a cover thickness $T_c$ of 1.5 mm in depth. The cover 104 includes, for example, a total of three magnetic elements 132b that align with the magnetic elements 132a of the base 102. This enables the cover 104 to be magnetically secured to the base 102 based in one of a defined set of orientations via the polarity of the magnetic elements 132a, 132b. By properly aligning the plurality of the magnetic elements 132a, 132b, the cover 104 may be magnetically secured to the base 102 in, for example, one of two different orientations. Depending on the orientation, different set of human- and/or machine-readable markings or information 108a, 108b carried by the cover 104 may be visible, some of the set of human- and/or machine-readable markings or information 108a, 108b displayed adjacent respective portions of the diagnostic assay test strip 106a, 106b. Additionally or alternatively, the cover 104 may expose indicia found on the surface of the base 102, that is only exposed for selected orientations of the cover 104 when attached to the base 102.

Figure 3:
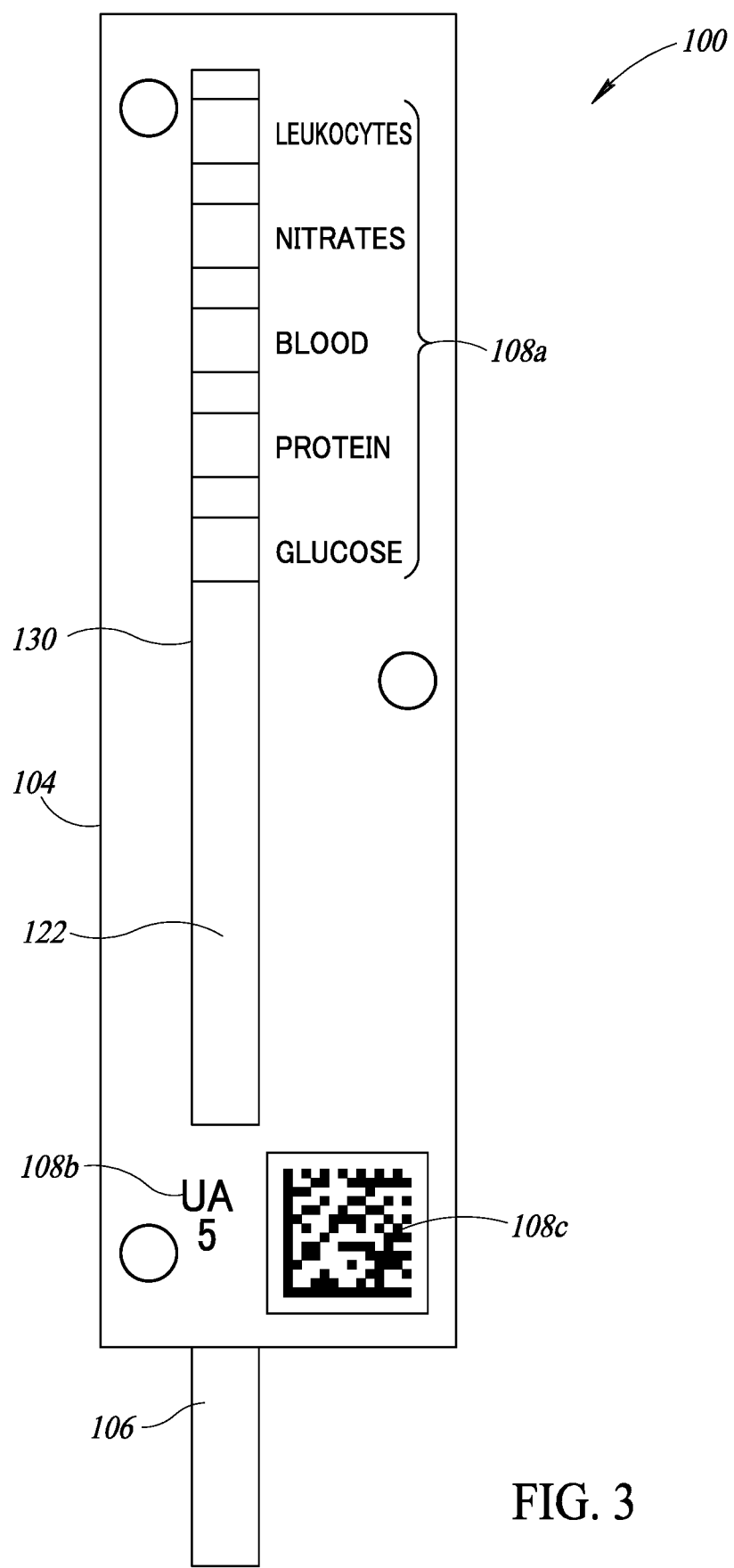
FIG. 3 is a top plan view of the cassette and diagnostic assay test strip of FIG. 1, with the cover in the first orientation with a first set of human- and/or machine-readable markings or information visible and with at least some of the first set of human- and/or machine-readable markings or information aligned with respective portions of a first type of diagnostic assay test strip.

FIG. 3 shows the cassette 100 with a first type of diagnostic assay test strip 106a received therein.

FIG. 3 better illustrates exemplary human- and/or machine-readable markings or information carried by cover 104, which includes a first number of respective identifiers for specific assays or tests, collectively 108a, a type identifier 108b that identifies the type of diagnostic assay test strip 106, and a machine-readable barcode or 2-D code symbol 308c that encodes information which is optically readable. The encoded information can identify the type of diagnostic assay test strip, and/or other information related to the assay or testing.

To change orientations of the cover 104 of the cassette 100 illustrated in FIG. 3, the user rotates the cover 104 by 180° about a lateral axis (i.e., extending along the width of the cover 104 and centered along the length of the cover 104). Where the channel 122 and window 130 are centered, to change orientations of the cover, the user simply rotates the cover 180° about a longitudinal axis (i.e., extending along the length of the cover and centered along the width of the cover).

Figure 4:
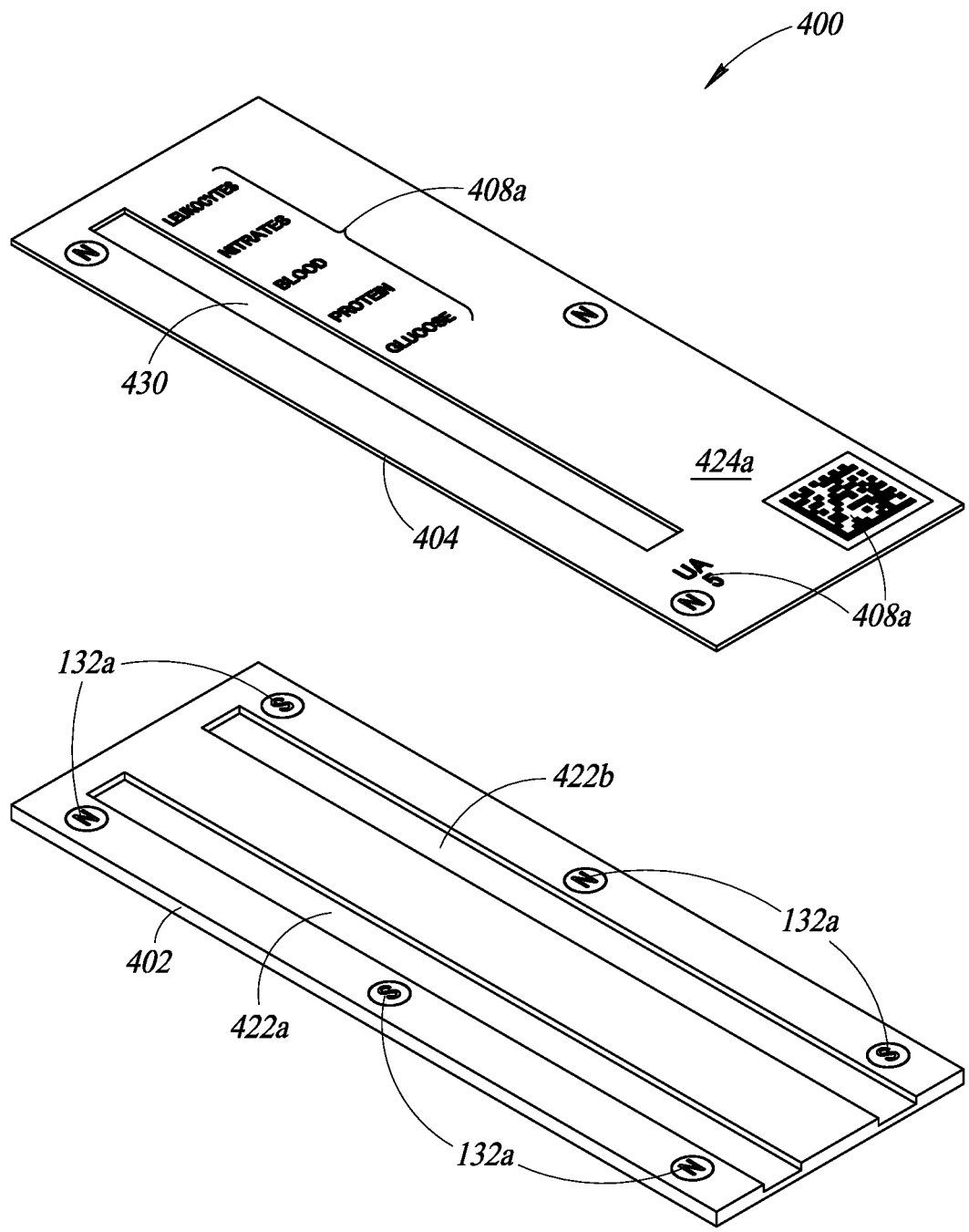
FIG. 4 is an isometric view of a cassette having a second channel in the first face of the base, shown with the cover in a first orientation with a first set of human- and/or machine-readable markings or information visible and with at least some of the first set of human- and/or machine-readable markings or information aligned with respective portions of a first type of diagnostic assay test strip, according to at least one illustrated embodiment.

FIG. 4 shows a cassette 400 having a base 402 and a cover 404 for use with a first type of diagnostic assay test strip 106 (FIG. 6), the cover 404 in a first orientation with respect to the base 402 with a first set of human- and/or machine-readable markings or information, collectively 408a, carried by a first face 424a of cover 404, visible and with at least some of the first set of human- and/or machine-readable markings or information positioned to align with respective portions of the first type of diagnostic assay test strip when received in the cassette 400 with the cover 404 secured thereto, according to at least one illustrated embodiment.

Figure 5:
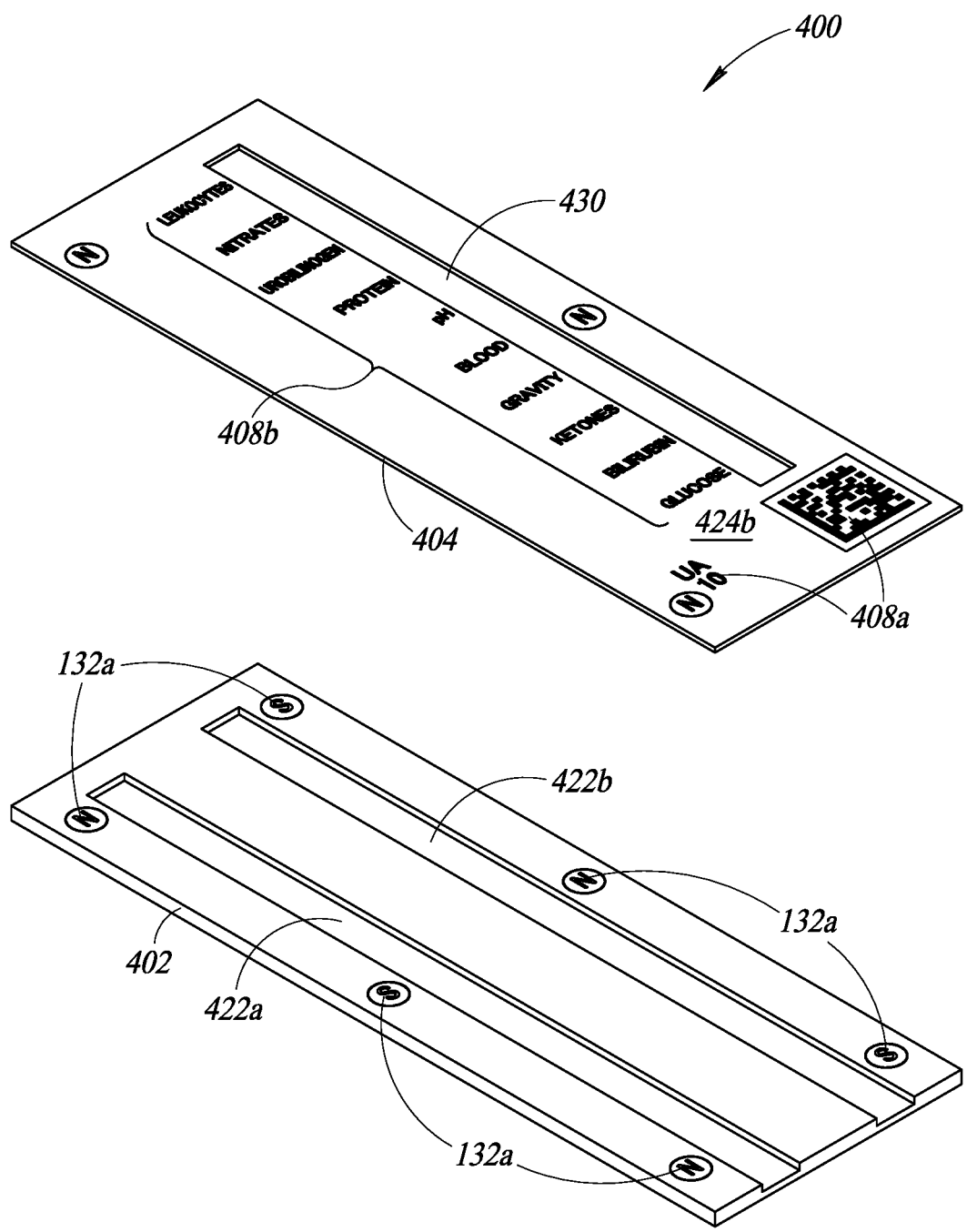
FIG. 5 is an isometric view of the cassette of FIG. 4, and a second type of diagnostic assay test strip, shown with the cover in a second orientation with a second set of human- and/or machine-readable markings or information visible and with at least some of the second set of human- and/or machine-readable markings or information aligned with respective portions of a second type of diagnostic assay test strip, according to at least one illustrated embodiment.

FIG. 5 shows the cassette 400 for use with a second type of diagnostic assay test strip 106 (FIG. 6), the cover 402 in a second orientation with respect to the base 402, with a second set of human- and/or machine-readable markings or information, collectively 408b, carried by a second face 424b of cover 404, visible and with at least some of the second set of human- and/or machine-readable markings or information positioned to align with respective portions of the second type of diagnostic assay test strip when received in the cassette 400 with the cover 404 secured thereto.

The cassette 400 is similar to the cassette 100 (FIGS. 1 and 2), however the base 402 has a first and a second channel 422a, 422b are laterally offset along a width of the base, and the window 430 of the cover 404 is laterally offset along a width of the cover from a centerline thereof to be alternatingly in registration with the first channel 422a when in a first orientation with respect to the base 402 and in registration with the second channel 422b when in a second orientation with respect to the base 402.

As illustrated, various magnetic elements (i.e., magnets, ferrous metal) 132a, 132b are positioned on the base 102 and cover 104, respectively, which properly align the cover 104 with respect to the base 102 in each of correct or acceptable orientations of the cover 120 with respect to the base 102. Alternatively, other fasteners can be employed, for instance snaps, detents, pins and receptacles, slots and tabs.

To change orientations of the cover 404 of the cassette 100 illustrated in FIGS. 1 and 2, the user simply rotates the cover 404 by 180° about a longitudinal axis (i.e., extending along the length of the cover 404 and centered along the width of the cover 404).

Figure 6:
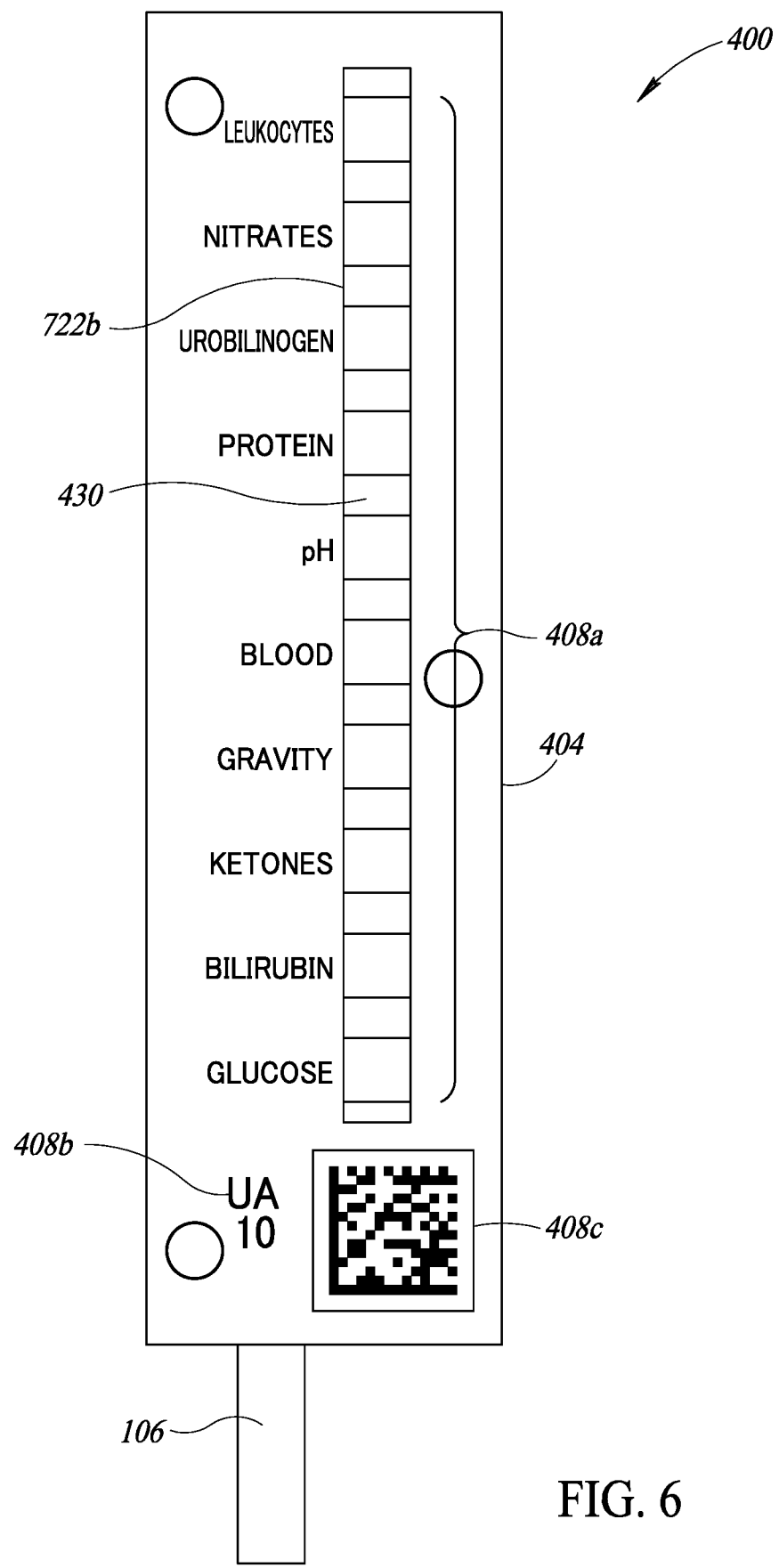
FIG. 6 is a top plan view of the cassette and diagnostic assay test strip of FIG. 5, with the cover in the second orientation with a second set of human- and/or machine-readable markings or information visible and with at least some of the second set of human- and/or machine-readable markings or information aligned with respective portions of a second type of diagnostic assay test strip.

FIG. 6 shows the cassette 400 of FIGS. 4 and 5, better illustrating exemplary human- and/or machine-readable markings or information carried by cover 404, which includes a first number of respective identifiers for specific assays or tests, collectively 408a, a type identifier 408b that identifies the type of diagnostic assay test strip 406, and a machine-readable barcode or 2-D code symbol 408c that encodes information which is optically readable. The encoded information can identify the type of diagnostic assay test strip, and/or other information related to the assay or testing.

Figure 7:
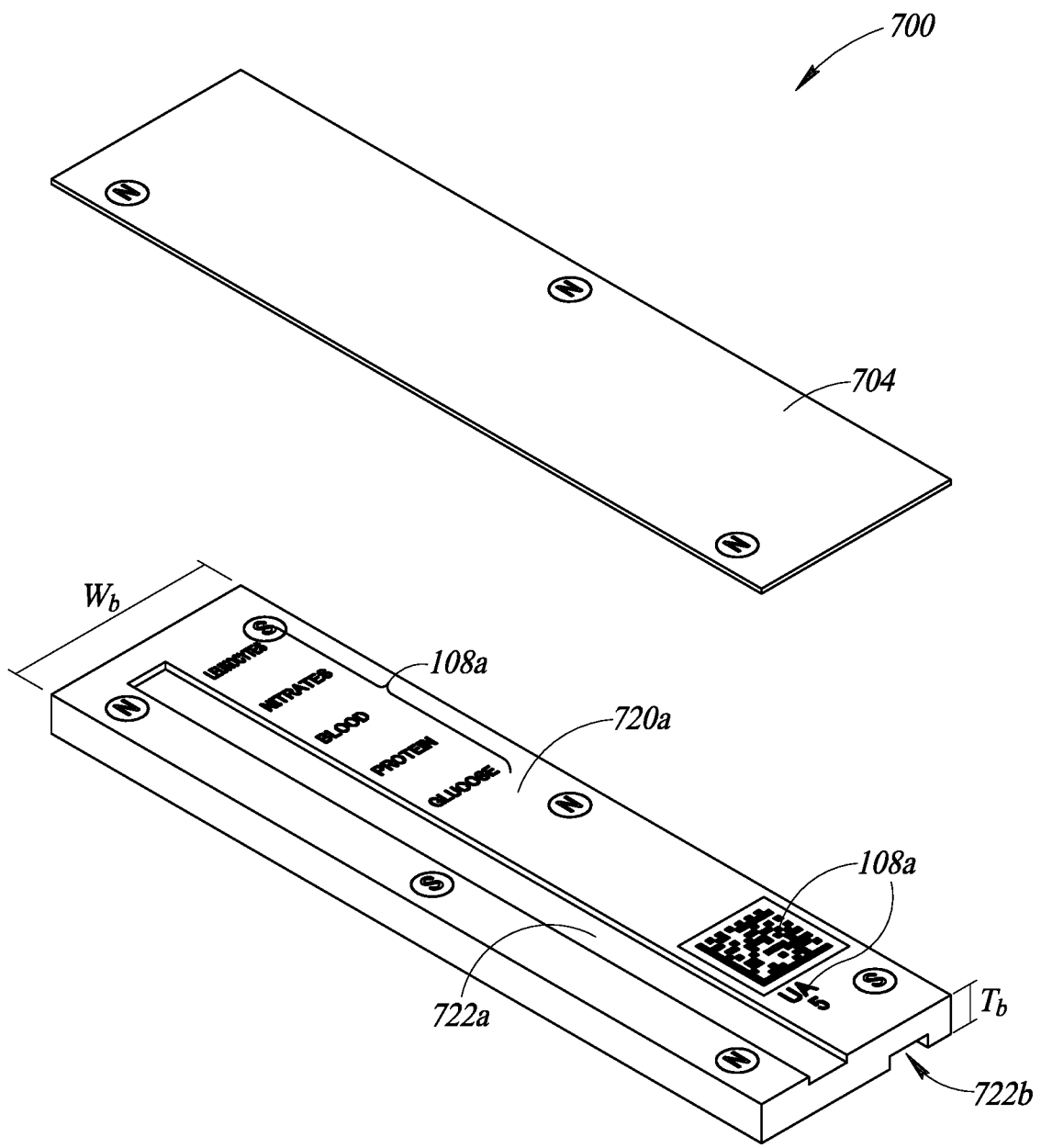
FIG. 7 is an isometric view of the cassette having a base that bears a first set of human- and/or machine-readable markings or information carried by a first face of the base, and a second set of human- and/or machine-readable markings or information carried by a second face of the base, the second face opposed across a thickness of the base from a first face thereof, and a transparent cover selectively positionable over the first or the second face of the base, according to at least one illustrated embodiment.

FIG. 7 shows a cassette 700 having a base 702 and a transparent cover 704 for use with diagnostic assay test strips (not illustrated in FIG. 7), the base 702 shown in a first orientation with a first set of human- and/or machine-readable markings or information, collectively 108a, visible and with at least some of the first set of human- and/or machine-readable markings or information positioned to align with respective portions of a diagnostic assay test strip when received in the cassette 700, according to at least one illustrated embodiment.

In contrast to previously described implementations, the cassette 700 has a first channel 722a formed in a first face 720a and a second channel 722b formed in a second face 720b, the second face 720b opposed to the first face 720a across a thickness $T_b$ of the base 702. The first and the second channels 722a, 722b may be laterally offset along a width $W_b$ of the base 702. Also contrast to previously described implementations, the entire cover 704 is transparent.

As illustrated, various magnetic elements (i.e., magnets, ferrous metal) 132a, 132b are positioned on the base 702 and cover 704, respectively, which properly align the cover 704 with respect to the base 702 in registration with one another. Alternatively, other fasteners can be employed, for instance snaps, detents, pins and receptacles, slots and tabs.

To change orientations, the user simply rotates the base 702 by 180° about a longitudinal axis (i.e., extending along the length of the base 702 and centered along the width of the base 702) so the desired set of human- and/or machine-readable markings or information, collectively 108a is facing up, and secures the cover 704 to the upward facing face 720a, 720b of the base 702.

Figure 8:
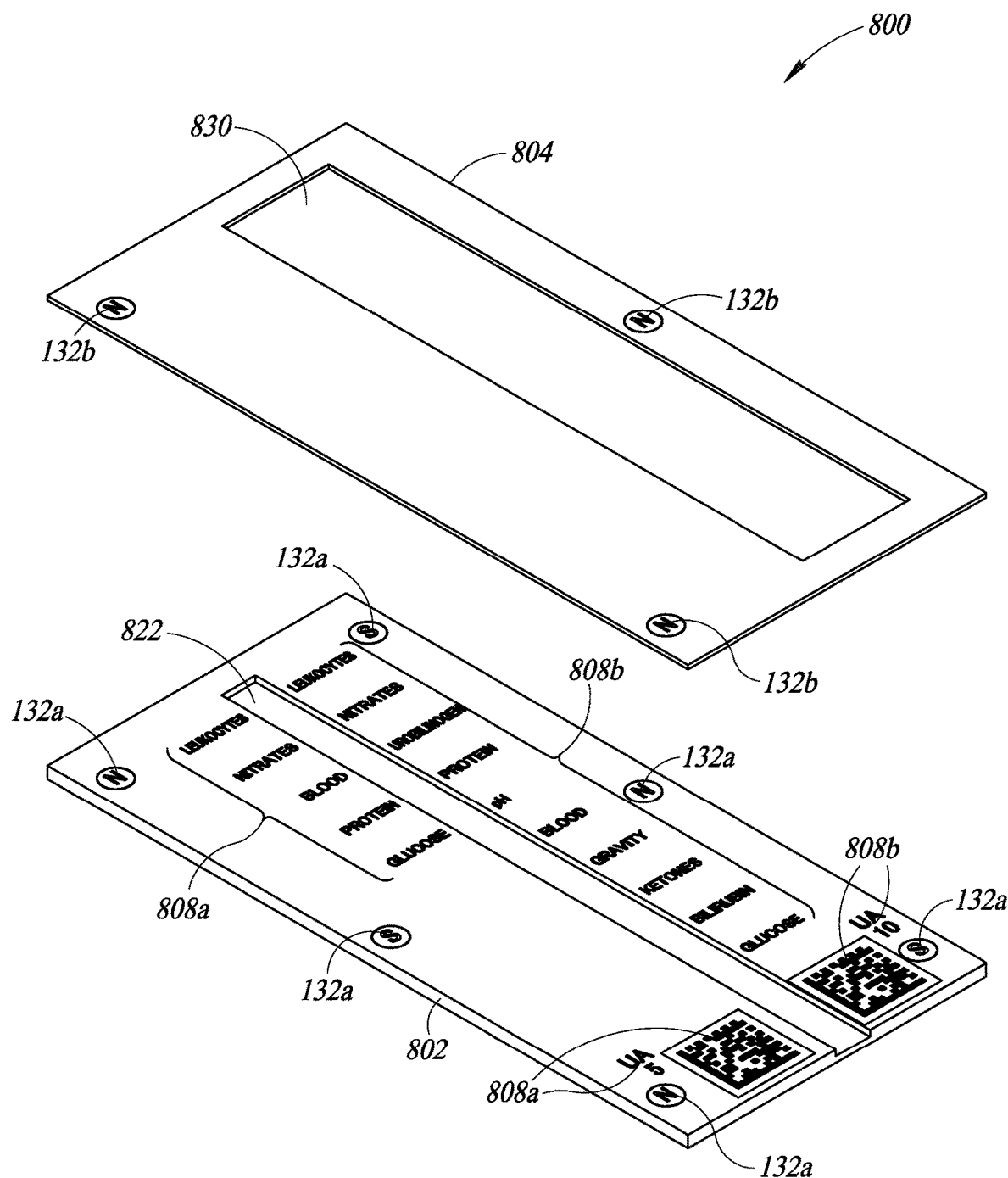
FIG. 8 is an isometric view of a cassette having a base with a channel, the base which bears a first set of human- and/or machine-readable markings or information carried by a first face of the base laterally disposed to a first side of the channel, and a second set of human- and/or machine-readable markings or information carried by the first face of the base laterally disposed to a second side of the channel, and a cover having a window to expose the channel and selectively expose either the first or the second set of human- and/or machine-readable markings or information, according to at least one illustrated embodiment.

FIG. 8 shows a cassette 800 for use with a diagnostic assay test strips (not illustrated in FIG. 8), including a base 802 that has a channel 822 and a first and a second set of human- and/or machine-readable markings or information 808a, 808b opposed across the channel 822 from one another. The cassette also includes a cover 804 with a window 830, showing in a first orientation with respect to the base 802. When secured to the base 802 in the first orientation and in registration therewith, the window encompasses the channel 822 and only one set of the human-and/or machine-readable markings or information 808a. When secured to the base 802 in the second orientation and in registration therewith, the window encompasses the channel 822 and only the other set of the human- and/or machine-readable markings or information 808b. As in the other implementations, such allows one cassette to be used with two different types of diagnostic assay test strips, with the corresponding functional information readily readable.

As illustrated, various magnetic elements (i.e., magnets, ferrous metal) 132a, 132b are positioned on the base 802 and cover 804, respectively, which properly align the cover 804 with respect to the base 802 in registration with one another. Alternatively, other fasteners can be employed, for instance snaps, detents, pins and receptacles, slots and tabs.

To change orientations, the user simply rotates the cover 804 by 180° about a longitudinal axis (i.e., extending along the length of the cover 804 and centered along the width of the cover 804), and secures the cover 804 to the base 802 with the desired or correct human- and/or machine-readable markings or information 108a visible through the window 830.

In the various implementations and embodiments described above, at least one of a plurality of magnetic elements 132a is carried by the base and at least one of the magnetic elements 132b is likewise carried by the cover. The magnetic elements 132a carried by the base are arranged with respect to the magnetic elements 132b carried by the cover to magnetically releasably retain the cover to the base. This provides proper orientation of the cover to the base. In the various embodiments other than that of FIG. 7, the magnetic elements 132a are arranged with respect to the magnetic elements 132b to magnetically releasably retain the cover to the base only in defined orientations (e.g., the first and the second orientations), and not in any other orientation. That is, in the first orientation, at least some of the first set of human- and/or machine-readable markings align with respective indication lines of a first type of diagnostic assay test strip. In the second orientation, at least some of the first set of human- and/or machine-readable markings align with respective indication lines of a second type of diagnostic assay test strip, the second type of diagnostic assay test strip for example having a fewer total number of indication lines than a total number of indication lines of the first type of diagnostic assay test strip.

The magnetic elements 132a, 132b may be magnets. The magnets may include a number of pieces of ferrous metal. In addition or alternatively, non-magnetic elements may be used in lieu of or in combination with the magnetic elements to properly secure the cover to the base. For example, the cover may include various structures that enable it to properly snap in place with the base only when the proper connection elements align. Similarly, adhesives or hook and loop fastener Velcro® may be used, particularly for single use cassette devices.

In this or any other implementation, when a cassette is used with a specimen analysis system or machine reader, the specimen analysis system or machine reader may be used to automatically or autonomously read machine-readable information carried by the cover and/or the base of the cassette. Such optically encoded data/indicia may include one of or a combination of machine readable symbols such as barcode symbols, matrix or area code symbols, stacked code symbols, and the like. The machine-readable data can include the type of test strip being used, the manufacturer thereof, and any other information considered pertinent or desired. Other data and indicia may be read using alternative methods and systems in addition to the optically encoded data or indicia. Such systems are described in detail in U.S. Pat. No. 8,446,463 which is incorporated herein by reference in its entirety. The specimen analysis system or machine reader can employ the read information in properly automatically performing analysis of the diagnostic assay test strip, for example selecting between a variety of algorithms and/or parameters and determining assay or test results based on the detected optical properties or characteristics of the diagnostic assay test strip (e.g., presence or absence of lines, color of lines) using the selected algorithm and/or based on the selected parameters. This can allow a single specimen analysis system or machine reader to autonomously be used to read a variety types of diagnostic assay test strip, without a need for an end user to program the specimen analysis system or machine reader according to the particular type of diagnostic assay test strip.

Any type of indicia may be used with the cassette disclosed herein. Tactile indicia, indicia sensitive to particular wavelengths, e.g., ultraviolet and infrared, temperature sensitive indicia, and the like. Further, the indicia may be displayed on both the base and the cover using various modalities, including, but not limited to ink, raised indicia, powered displays, e.g., organic light emitting diodes, active matrix light emitting diodes, and the like.

Finally, by using the cassette described herein, the test strip may be held firmly in place within the channel. The channel and the cover can hold the test strip so that an accurate scan by a reader may be made. Further, both the channel and the cover may be used to prevent cross contamination of the test strip during use.

Those of skill in the art will recognize that many of the methods or algorithms set out herein may employ additional acts, may omit some acts, and/or may execute acts in a different order than specified.

The various embodiments described above can be combined to provide further embodiments. To the extent that they are not inconsistent with the specific teachings and definitions herein, all of the commonly assigned U.S. patents, U.S. patent application publications, U.S. patent applications referred to in this specification, including but not limited to U.S. Pat. No. 8,446,463, U.S. patent application Ser. No. 15/014,920, filed Feb. 3, 2016; U.S. Provisional Patent Application No. 62/395,150, filed Sep. 15, 2016; and U.S. Provisional Patent Application No. 62/111,418, filed Feb. 3, 2015 are incorporated herein by reference, in their entirety. Aspects of the embodiments can be modified, if necessary, to employ systems, circuits and concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A cassette to removably hold assay strips, comprising:
   a base, the base having a first face and a second face, the second face opposed across a thickness of the base from the first face, the base having a first channel in the first face that extends along at least a portion of the base, the first channel having a width, a length and a depth, at least the width and the depth of the first channel sized to closely removably receive an assay strip therein; and
   a cover, the cover having a first face and a second face, the second face opposed across a thickness of the cover from the first face, the cover releasably securable to the base in at least two orientations to alternatively expose a first set of markings and a second set of markings, the first and the second set of markings carried by at least one of the cover or the base, the first set of markings indicative of a first type of assay strip and the second set of markings indicative of a second type of assay strip, the second set of markings different from the first set of markings, the two orientations including a first orientation in which the first face of the cover is exposed and the second face of the cover is adjacent one of the first or the second faces of the base, and a second orientation in which the second face of the cover is exposed and the first face of the cover is adjacent one of the first or the second faces of the base.

2. The cassette of claim 1 wherein the base has a length and a width, and the first channel extends along the length of the base.

3. The cassette of claim 2 wherein the cover has a window and an opaque frame about the window, the window transparent to light of at least one range of wavelengths, and the first set of markings are carried on the first face of the cover and the second set of markings are carried on the second face of the cover.

4. The cassette of claim 3 wherein the window of the cover is in registration with the first channel when the cover is releasably secured to the base in both the first and the second orientations.

5. The cassette of claim 1 wherein the base has a length and a width, and the first channel extends along the length of the base and is centered with respect to the width of the base.

6. The cassette of claim 1 wherein the base has a length and a width, and has a second channel in the first face of the base that extends along at least a portion of the length of the base, the second channel having a width, a length and a depth, at least the width and the depth of the second channel sized to closely removably receive an assay strip therein, the first channel laterally disposed in a first direction from a centerline of the base and the second channel laterally disposed in a second direction from the centerline of the base, the second direction opposite the first direction.

7. The cassette of claim 6 wherein the cover has a window and an opaque frame about the window, the window transparent to light of at least one range of wavelengths, and the first set of markings are carried on the first face of the cover and the second set of markings are carried on the second face of the cover, the window spaced relatively towards a first lateral edge of the cover with respect to a second lateral edge of the cover, the second lateral edge of the cover opposed across a width of the cover from the first lateral edge of the cover.

8. The cassette of claim 7 wherein the window of the cover is in registration with the first channel when the cover is releasably secured to the base in the first orientation, and the window of the cover is in registration with the second channel when the cover is releasably secured to the base in the second orientation.

9. The cassette of claim 1 wherein the base has a length and a width, and has a second channel in the second face of the base that extends along at least a portion of the length of the base, the second channel having a width, a length and a depth, at least the width and the depth of the second channel sized to closely removably receive an assay strip therein, the first channel laterally disposed in a first direction from a centerline of the base and the second channel laterally disposed in a second direction from the centerline of the base, the second direction opposite the first direction.

10. The cassette of claim 9 wherein the cover is transparent to light of at least one range of wavelengths, and the first set of markings are carried on the first face of the base and the second set of markings are carried on the second face of the base.

11. The cassette of claim 1 wherein the first set of markings are carried on the first face of the base, a number of the first set of markings spaced laterally to a first side of the first channel, and the second set of markings are carried on the first face of the base, a number of the second set of markings spaced laterally to a second side of the first channel, the second side opposed across the first channel from the first side of the first channel.

12. The cassette of claim 11 wherein the cover has a window and an opaque frame about the window, the window transparent to light of at least one range of wavelengths, and the window laterally disposed in a first direction from a centerline of the cover.

13. The cassette of claim 12 wherein the window of the cover is in registration with the first channel and the number of the first set of markings that are spaced laterally to the first side of the first channel when the cover is releasably secured to the base in the first orientation to expose the first channel and the number of the first set of markings and occlude the number of the second set of markings in the first orientation, and the window of the cover is in registration with the first channel and the number of the second set of markings that are spaced laterally to the second side of the first channel when the cover is releasably secured to the base in the second orientation to expose the first channel and the number of the second set of markings and occlude the number of the first set of markings in the second orientation.

14. The cassette of claim 1 wherein the first set of markings include a first number of markings that extend along at least a portion of the window and which align with respective portions of the first type of assay strip when the first type of assay strip is received in the first channel, and the second set of markings include a second number of markings that extend along at least a portion of the window and which align with respective portions of the second type of assay strip when the second type of assay strip is received in the first channel.

15. The cassette of claim 13 wherein the first set of markings include a number of human-readable markings that are laterally offset to a first side of the window and the second number of markings include markings that are laterally offset to a second side of the window, the second side opposed across the window from the first side.

16. The cassette of claim 1 wherein the first set of markings include a number of human-readable markings that are laterally offset to a first side of the window and the second number of markings include markings that are laterally offset to a second side of the window, the second side opposed across the window from the first side.

17. The cassette of claim 1 wherein the first set of markings include a first machine-readable symbol that encodes a first set of machine-readable information, and the second set of markings include a second machine-readable symbol that encodes a second set of machine-readable information, the second set of machine-readable information different from the first set of machine-readable information.

18. The cassette of claim 1 wherein the cover is a transparent substrate and the frame is an opaque layer carried by the transparent substrate, and the window provides environmental protection to an assay strip removably received in the first channel.

19. The cassette of claim 1 further comprising:
a plurality of magnetic elements, at least one of the magnetic elements carried by the base and at least one of the magnetic elements carried by the cover, the magnetic elements carried by the base arranged with respect to the magnetic elements carried by the cover to magnetically releasably retain the cover to the base.

20. The cassette of claim 1, further comprising:
a plurality of magnetic elements, at least one of the magnetic elements carried by the base and at least one of the magnetic elements carried by the cover, the magnetic elements carried by the base arranged with respect to the magnetic elements carried by the cover to magnetically releasably retain the cover to the base only in the first and the second orientations, and not in any other orientation, where: i) in the first orientation, a plurality of markings of the first set of markings align with respective indication lines of a first type of assay strip, and ii) in the second orientation, a plurality of markings of the second set of markings align with respective indication lines of a second type of assay strip, the second type of assay strip having a fewer total number of indication lines than a total number of indication lines of the first type of assay strip.

21. The cassette of claim 20 wherein the plurality of magnetic elements include a number of magnets.

22. The cassette of claim 21 wherein the plurality of magnetic elements include a number of pieces of ferrous metal.

23. The cassette of claim 1 wherein the base is a rectangular substrate with a length and a width, and the cover is a rectangular substrate with a length and a width, the length and the width of the cover being respectively equal to the length and the width of the base.

24. The cassette of claim 1 wherein the first channel extends to an end of the base and the length of the first channel is sized such that a portion of an assay strip received in the first channel extends partially outward from the end of the base.

* * * * *